US012778858B2

(12) United States Patent
Stine et al.

(10) Patent No.: US 12,778,858 B2
(45) **Date of Patent: *Nov. 3, 2026**

(54) MASKING COMPOSITIONS FOR MILLED LITHIUM-SILICATE GLASS-CERAMIC DENTAL RESTORATIONS AND METHOD FOR MAKING SAME

(71) Applicant: Jensen Industries Inc., North Haven, CT (US)

(72) Inventors: David J. Stine, Islamorada, FL (US); Donald F. Cornell, Lakeway, TX (US); Yoonho Jun, Weatogue, CT (US)

(73) Assignee: JENSEN INDUSTRIES INC., North Haven, CT (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/883,441

(22) Filed: Sep. 12, 2024

(65) Prior Publication Data

US 2025/0000748 A1 Jan. 2, 2025

Related U.S. Application Data

(62) Division of application No. 16/951,134, filed on Nov. 18, 2020, now Pat. No. 12,102,698.

(60) Provisional application No. 62/936,928, filed on Nov. 18, 2019.

(51) Int. Cl.

| | |
|---|---|
| ***A61K 6/833*** | (2020.01) |
| ***A61K 6/65*** | (2020.01) |
| ***A61K 6/71*** | (2020.01) |
| ***A61K 6/77*** | (2020.01) |
| ***A61K 6/78*** | (2020.01) |
| ***A61K 6/887*** | (2020.01) |
| ***A61K 6/891*** | (2020.01) |
| ***C03C 1/04*** | (2006.01) |
| ***C03C 4/00*** | (2006.01) |
| ***C03C 8/00*** | (2006.01) |

(52) U.S. Cl.

CPC ................ *A61K 6/833* (2020.01); *A61K 6/65* (2020.01); *A61K 6/71* (2020.01); *A61K 6/77* (2020.01); *A61K 6/78* (2020.01); *A61K 6/887* (2020.01); *A61K 6/891* (2020.01); *C03C 1/04* (2013.01); *C03C 4/0021* (2013.01); *C03C 8/00* (2013.01)

(58) Field of Classification Search

CPC . A61K 6/833; A61K 6/77; A61K 6/65; A61K 6/891; C03C 1/04; C03C 4/0021

See application file for complete search history.

(56) References Cited

U.S. PATENT DOCUMENTS

| | | | |
|---|---|---|---|
| 4,806,383 A | 2/1989 | Poltz | |
| 6,797,048 B2 | 9/2004 | Hoshikawa et al. | |
| 9,326,917 B2 | 5/2016 | Maletz et al. | |
| 2003/0138757 A1 | 7/2003 | Cohen et al. | |
| 2009/0074945 A1 * | 3/2009 | Yilmaz | C03C 4/0021 106/35 |
| 2017/0189143 A1 | 7/2017 | Wolz | |

FOREIGN PATENT DOCUMENTS

| | | | |
|---|---|---|---|
| EP | 1245548 | * | 2/2002 |
| EP | 1245548 | A1 | 10/2002 |
| WO | 1995/032678 | A2 | 12/1995 |
| WO | 2006/042046 | A2 | 4/2006 |
| WO | 2019/199791 | A1 | 10/2019 |

OTHER PUBLICATIONS

Extended European Search Report mailed Nov. 24, 2023 in corresponding European Patent Application No. 20891183.4.

International Search Report mailed Feb. 11, 2021 in corresponding International Patent Application No. PCT/US2020/060971.

* cited by examiner

*Primary Examiner* — Nathan T Leong

(74) *Attorney, Agent, or Firm* — Troutman Pepper Locke LLP

(57) ABSTRACT

Masking compositions useful for dental restoration, particularly masking compositions used as a coating to mask the unnatural color of milled lithium-silicate glass-ceramic dental restorations in soft states before crystallization cycle, and method of making same. Some embodiments relate to masking compositions comprising at least one glaze powder, at least one opacifier, and at least one colorant. Some embodiments relate to coating, drying, cooling, characterizing, and firing of dental restorations.

20 Claims, No Drawings

MASKING COMPOSITIONS FOR MILLED LITHIUM-SILICATE GLASS-CERAMIC DENTAL RESTORATIONS AND METHOD FOR MAKING SAME

CROSS REFERENCE TO RELATED APPLICATIONS

This application is a divisional of U.S. patent application Ser. No. 16/951,134, filed Nov. 18, 2020, which claims the benefit of U.S. Provisional Patent Application Ser. No. 62/936,928, filed on Nov. 18, 2019, the entire contents of each of which are hereby incorporated by reference herein.

BACKGROUND

Lithium-silicate glass ceramics are formed into dental restorations by a variety of methods, one of which involves using modern CAD/CAM techniques to machine the restoration out of a metastable "soft state" glass-ceramic block. After machining, the milled restoration is subjected to a crystallization firing cycle that transforms the material to its high strength and stable crystal structure using heat.

During this crystallization firing cycle, the appearance of the material, as well as its mechanical properties, changes. The metastable "soft state" material does not generally look like a dental material. Lithium silicates in their machinable, metastable conditions may appear blue and highly opaque (e.g., e.max CAD, Ivoclar N.A.), or they may look like very transparent amber (e.g., Suprinity PC, Vita Zahnfabrik). Once the restoration is subject to this crystallization firing cycle, the base color of the final restoration is established, and the dentist or dental technician can apply stains, colors, and glazes to better match the patient's shade and make the restoration appear more like a natural tooth.

One of the problems with the method described above is that most machined glass-ceramic restorations are made "chairside" and not in laboratory setting. In other words they are mostly made at the dentist's office while the patient is in the office. Therefore, there is a greater need for efficiency and speed for "chairside" restorations than for laboratory fabricated restorations. The above described workflow requires that the milled restoration be fired at least twice: once on the crystallization firing cycle, and again on the glazing firing cycle after color adjustment, characterization, and glazing. Each firing cycle takes about 15-20 minutes and, accordingly, it would be desirable to reduce the number of firing cycles, thereby reducing the amount of time the patient is waiting for their restoration.

Some manufacturers of lithium-silicate glass-ceramic blocks provide instructions that enable users to crystallize, modify color, and glaze on a single cycle. The dentist or technician needs to apply stains and color modifiers to a lithium-silicate glass-ceramic restoration that is in the "soft state", e.g. an opaque blue color or perhaps a clear amber glassy looking material. Due to this decidedly un-toothlike appearance, it is difficult even for a skilled technician to customize a restoration because they are essentially guessing at what the final color is going to be.

Accordingly, there is a need for masking and color matching agents for milled lithium-silicate glass-ceramic dental restorations and better method for making same.

SUMMARY

In some embodiments, a masking composition suitable to coat a lithium-silicate glass-ceramic dental restoration in soft state is disclosed. In these embodiments, the masking composition comprises at least one glaze powder, at least one opacifier, and at least one colorant, wherein the opacifier and colorant are designed to disappear during crystallization cycle.

In some embodiments, the at least one glaze powder comprises about 5 wt. % to about 85 wt. % of the masking composition.

In some embodiments, the at least one opacifier comprises about 0.1 wt. % to about 40 wt. % of the masking composition. In some embodiments, the at least one glaze powder and at least one opacifier have a ratio between about 1:0.5 to about 1:0.01. In some embodiments, the at least one opacifier is selected from the group consisting of zinc oxide, titania, tin oxide, or combinations thereof.

In some embodiments, the at least one colorant comprises about 0.01 wt. % to about 10 wt. % of the masking composition. In some embodiments, the colorant is an organic dye, an organic pigment, or a combination thereof. In some embodiments, the at least one colorant is selected from the group consisting of yellow 5, yellow 23, red 40, a neutral grey dye (for example, Procion™ MX Neutral Grey), a jet black dye (for example, Procion™ MX Jet Black 5), or combinations thereof.

In some embodiments, the masking composition comprises at least one polymer. In some embodiments, the at least one polymer comprises about 0.1 wt. % to about 80 wt. % of the masking composition. In some embodiments, the at least one polymer can be a polymerizable monomer, a polymerizable oligomer, polymerizable polymer, or a combination thereof. In some embodiments, the polymerizable monomer, the polymerizable oligomer and the polymerizable polymer are polymerizable/curable with light curing, thermal curing, or a combination thereof.

In some embodiments, the at least one polymer is added directly or as a polymer solution to the masking composition. In some embodiments, the at least one polymer is selected from the group consisting of polyethylene glycol, polypropylene glycol, polyacrylate, polymethacrylate, polyvinyl alcohol, polyvinyl butyral, polylactic acid, or combinations thereof.

In some embodiments, the masking composition comprises at least one solvent. In some embodiments, the at least one solvent comprises equal to or less than about 95 wt. % of the masking composition. In some embodiments, the at least one solvent is selected from the group consisting of water, methanol, ethanol, propanol, isopropanol, ethyl acetate, hexane, toluene, ethylene glycol, propylene glycol, butylene glycol, glycerol, polyethylene glycol, polypropylene glycol, or combinations thereof.

In some embodiments, a method for making a lithium-silicate glass-ceramic dental restoration is disclosed. In these embodiments, the method comprises mixing a masking composition to form a paste and coating with the paste the lithium-silicate glass ceramic to form a coated lithium-silicate glass-ceramic dental restoration.

In some embodiments, a method for making a lithium-silicate glass-ceramic dental restoration comprising drying the coated lithium-silicate glass-ceramic dental restoration using heat is disclosed. In some embodiments, the drying temperature is in a range of about 20° C. to about 450° C. In some embodiments, the drying time is in a range of about 5 seconds to about 300 seconds.

In some embodiments, a method for making a lithium-silicate glass-ceramic dental restoration comprising the step of cooling the coated lithium-silicate glass-ceramic dental restoration is disclosed.

In some embodiments, a method for making a lithium-silicate glass-ceramic dental restoration comprising the step of applying a characterization on a coated lithium-silicate glass-ceramic dental restoration is disclosed. In some embodiments, the characterization is selected from the group consisting of glazes, stains, structural compounds, or combinations thereof.

In some embodiments, a method for making a dental restoration comprising crystallizing the coated and stained lithium-silicate glass ceramic is disclosed. In some embodiments, the crystallization temperature in a range of about 500° C. to about 1,000° C.

DETAILED DESCRIPTION

It will be appreciated that for clarity, the following discussion will describe various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. One of ordinary skill in the art will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

Various terms are used herein consistent with their common meanings in the art. The following terms are defined below for clarity.

The term "about" as used herein denotes a variation of at most 10% around a numerical value, unless context dictates otherwise.

The term "Ceramic" as used herein shall include ceramics and synthetic ceramics unless otherwise indicated.

"Low-fusing" as used herein generally refers to ceramics that fuse at temperatures below normal firing temperatures. In some embodiments, low-fusing temperatures are 850° C., 800° C., or below.

All percentages referred to herein are percent by weight, unless otherwise indicated.

The term "CAD" as used herein refers to computer-aided design techniques that can be used in the field of dentistry, unless context dictates otherwise.

The term "CAM" as used herein refers to computer-aided manufacturing techniques that can be used in the field of dentistry, unless context dictates otherwise.

The masking compositions disclosed herein comprise at least one glaze powder, at least one opacifier, and at least one colorant, such that when applied to a lithium-silicate restoration, an opaque masking layer forms, mimicking the fired color of the underlying lithium silicate, but wherein the masking layer itself is not visible after firing (e.g. crystallization). The masking composition may further comprise a solvent and/or a polymer. In some embodiments, the masking composition may be formed into a powder, paste, or formulated as a spray for application. The spray may be an aerosol spray.

After the masking composition is applied to the restoration, it dries to form a visible masking layer against which final characterizations (e.g. stains, glazes, etc.) may be applied. Once the characterizations are applied, and the restoration is fired at crystallization temperatures, the masking layer causes a minimum of shade shift or no shade shift. The masking layer partially, or in some cases completely, disappears during the firing cycle; the opacifier dissolves partially or completely into the glaze and the colorant burns out, leaving the crown glazed and characterized with any applied ceramic stains.

Any suitable components may be used in the masking composition and as the masking layer, so long as upon firing they do not negatively affect the appearance of the restoration, that is, they essentially disappear. For example, many suitable colorants will be volatile at firing temperatures and will simply burn off during the firing process. As another example, suitable opacifiers and glaze powders can work in conjunction such that the opacifier dissolves into the glaze during firing, resulting in a transparent appearance. Other components, such as polymer provide strength and structure to the masking composition when it forms a masking layer and dissipate upon firing.

Components

The masking compositions for dental restoration disclosed herein comprise for instance and without limitation at least one glaze powder, at least one opacifier, and at least one colorant.

The glaze powder incorporated into the masking composition may be any of those generally available in the art. For example, the glaze powder can be ceramic based powder mixed with an appropriate solvent and other suitable materials, dyes, pigments, and structure building components.

Commercially available glazing material, such as Chemichl's glazing materials are also well-known in the art and also provide a desired coloring/optical effect and glaze finish upon firing. Differences in the compositions of these glazing materials generally create a different coloring or visual effect.

In some embodiments, the weight percent of the glaze powder in the masking composition is in a range of about 5 wt. % to about 99.9 wt. %, or about 5 wt. % to about 85 wt. %, or in a range of about 7 wt. % to about 82 wt. %, or in a range of about 10 wt. % to about 80 wt. %, or in a range of about 12 wt. % to about 75 wt. %.

The opacifier incorporated into the masking composition can be a natural or synthetic compound that is organic, inorganic, or a combination thereof. The opacifier is generally a white or pale solid or cream and used to decrease translucency and mask the glass ceramic substrate. Some illustrative examples of opacifier that can be used in some of the embodiments include the following: zinc oxide, titania, and tin oxide. In some embodiments, the weight percent of the opacifier of the masking composition is in a range of about 0.1 wt. % to about 40 wt. %, or in a range of about 0.2 wt. % to about 35 wt. %, or in a range of about 0.5 wt. % to about 30 wt. %, or in a range of about 1 wt. % to about 25 wt. %. In some embodiments, the ratio of the glaze powder to the opacifier (i.e., glaze powder:opacifier) is between about 1:0.5 to about 1:0.01, or is between about 1:0.45 to about 1:0.03, or is between about 1:0.40 to about 1:0.05. In some embodiments, the ratio of the glaze powder to the opacifier (i.e., glaze powder:opacifier) is about 1:0.5, or is about 1:0.45, or is about 1:0.4, or is about 1:0.3, or is about 1:0.2, or is about 1:0.1, or is about 1:0.08, or is about 1:0.04, or is about 1:0.01.

The colorant incorporated into the masking composition is not limited and is any material known in the art that is compatible with the masking. The colorant incorporated into the masking composition can be a natural or synthetic compound that is organic and can completely disappear during the crystallization cycle. The colorant is generally used to add color to the masking layer or mask the color of a milled lithium-silicate glass-ceramic dental restoration in soft state. The colorant can be a dye, a pigment, or a combination thereof. Some illustrative examples of colorant that can be used in some of the embodiments include the following: yellow 5 dye, yellow 23 dye, red 40 dye, a neutral grey dye (for example, Procion™ MX Neutral Grey dye), a jet black dye (for example, Procion™ MX Jet Black 5 dye).

In some embodiments, the colorant can be directly mixed in the masking composition or mixed with a solvent to form a colorant solution prior to be added to the masking composition. In some embodiments, the weight percent of the colorant from the colorant solution is in a range of about 0.1 wt. % to about 90 wt. % from the total weight of the colorant solution, or in a range of about 0.5 wt. % to about 80 wt. % from the total weight of the colorant solution, or in a range of about 0.8 wt. % to about 70 wt. % from the total weight of the colorant solution, or in a range of about 1 wt. % to about 60 wt. % from the total weight of the colorant solution. In some embodiments, the weight percent of the colorant solution from the masking composition is in a range of about 0.01 wt. % to about 95 wt. % from the total weight of the masking composition, or in a range of about 0.05 wt. % to about 90 wt. % from the total weight of the masking composition, or in a range of about 0.1 wt. % to about 80 wt. % from the total weight of the masking composition, or in a range of about 0.5 wt. % to about 70 wt. % from the total weight of the masking composition. In some embodiments, the weight percent of the colorant from the masking composition is in the range of about 0.1 wt. % to about 80 wt. % from the total weight of the masking composition. In some embodiments, the weight percent of the colorant from the masking composition is in a range of about 0.01 wt. % to about 70 wt. % from the total weight of the masking composition, or in a range of about 0.04 wt. % to about 65 wt. % from the total weight of the masking composition, or in a range of about 0.07 wt. % to about 60 wt. % from the total weight of the masking composition, or in a range of about 0.1 wt. % to about 50 wt. % from the total weight of the masking composition.

In some embodiments, the masking composition contains no solvent when the polymer is liquid and compatible with the colorant. In some embodiments, a solvent can be added to the masking composition to mix and/or dissolve the different components of the masking composition. The solvent added to the masking composition is not limited and is any material known in the art that is compatible with the masking composition. In some embodiments, the solvent is selected from the group consisting of water, methanol, ethanol, propanol, isopropanol, ethyl acetate, hexane, toluene, ethylene glycol, propylene glycol, butylene glycol, glycerol, polyethylene glycol, polypropylene glycol, or combination thereof. Other solvents can be used as long as the solvent is compatible with the masking composition. In some embodiments, the weight percent of solvent from the masking composition is in a range of about equal to or less than 95 wt. %, or in a range of about 0.1 wt. % to about 90 wt. %, or in a range of about 0.5 wt. % to about 85 wt. %, or in a range of about 1 wt. % to about 80 wt. %.

The polymer incorporated into the masking composition can be a natural or synthetic polymer that is organic, inorganic, or a combination thereof and can at least partially, or in some cases completely, disappear during the crystallization cycle. The polymer can be a polymerizable monomer, a polymerizable oligomer, or a combination thereof. The polymerizable monomer and the polymerizable oligomer can be with light curing, thermal curing, or combination thereof, polymer, random or block co-polymer, branched or hyperbranched polymer, capped polymer, functionalized polymer, or combinations thereof. The polymer is generally used to make the masking composition coating more robust. Illustrative examples of polymers that can be used in some of the embodiments include the following: polyether, polyester, polycarbonate, polyphosphate, or combinations thereof. In some embodiments, the polymer is selected from the group consisting of polyethylene glycol, polypropylene glycol, polyacrylate, polymethacrylate, polyvinyl alcohol, polyvinyl butyral, polylactic acid, or combinations thereof. In some embodiments, the polymer has a molecular weight in a range of about 200 g/mol to about 1,000,000 g/mol, or in a range of about 300 g/mol to about 500,000 g/mol, or in a range of about 400 g/mol to about 200,000 g/mol, or in a range of about 600 g/mol to about 100,000 g/mol, or in a range of about 1,000 g/mol to about 50,000 g/mol, or in a range of about 1,200 to about 20,000 g/mol. In some embodiments, the weight percent of the polymer from the masking composition is in a range of about 0.1 wt. % to about 80 wt. %, or in a range of about 0.5 wt. % to about 75 wt. %, or in a range of about 1 wt. % to about 70 wt. %, or in a range of about 2 wt. % to about 60 wt. %.

One of ordinary skill in the art will appreciate that different methods can be used to prepare the masking composition. In some embodiments, the masking composition is prepared by adding a liquid phase to a solid phase. In some embodiments, colorant can be added directly as a powder and/or solution. Polymer can be liquid or solid.

Some embodiments of the invention are directed to a masking composition used as a coating that masks the unnatural color of a milled lithium-silicate glass-ceramic dental restoration in soft state before crystallization cycle. As discussed in more detail below, in some embodiments, one or more colorants are introduced into a masking composition which is used to coat a dental restoration by, for instance: (i) adding to a glaze powder at least one opacifier and one colorant; (ii) mixing the masking composition to form a paste; (iii) coating with the paste the surface of a milled lithium-silicate glass-ceramic dental restoration in soft state; (iv) drying the coating from the dental restoration using heat; (v) cooling the coated dental restoration; and (vi) applying at least one layer of characterization on at least part of the coated dental restoration. In some embodiments, the polymer is liquid and no additional liquid solvent may not be necessary. In this case, drying and cooling may not be necessary. In some embodiments, light curing, thermal curing, or a combination thereof after coating is required to make the film sturdy. One of ordinary skill in the art will appreciate that application of the masking composition on the milled lithium-silicate glass-ceramic dental restoration prior to crystallization enables the technician responsible to better visualize what the ceramic would look like after crystallization, which facilitates the application of characterization such as without limitation glaze, stain, or combinations thereof. The masking layer, while visible prior to the crystallization firing cycle, becomes at least partially, or in some cases completely, transparent after the crystallization firing cycle, enabling the technician to create an accurate and esthetic restoration with a single firing cycle.

In some aspects, the masking layer is sufficiently robust to be at least partially, and in some cases completely, undisturbed (e.g. moved, diluted, mixed, etc.) when the technician applies subsequent characterizations. In some embodiments, at least one polymer can be added to the masking composition in order to increase of the robustness of the masking layer. One of ordinary skill in the art would appreciate that the added polymer can act as a matrix material in the masking layer. The monomers and oligomers from the polymer can be polymerized within the masking composition once applied to the milled lithium-silicate glass-ceramic dental restoration before, during, and/or after drying and/or cooling of the coated dental restoration, or combinations thereof. The polymerization of the monomers and oligomers can be achieved by, for instance and without limitation, light curing, thermal curing, or combinations thereof. When little or no polymer is in the masking layer, the layer which contains mainly particles such as glaze powder and opacifier can become partially, or in some cases completely, porous. The porous layer can then absorb liquid from the paste of the subsequent layer, which can make the application of the subsequent layers less homogeneous.

Properties and Uses of Masking Compositions

In some embodiments, the masking composition can be deposited on a glass ceramic to form a film or coating, wherein the glass ceramic can be a milled unit. The milled unit can be fabricated using a milling unit. One of ordinary skill in the art will appreciate that the milling unit can fabricate complete or partial dental restorations, wherein the fabrication can be based CAD/CAM systems. In some embodiments, the glass ceramic is selected from the group consisting of Ivoclar Vivadent IPS e.max CAD, Ivoclar N.A., Suprinity PC, Vita Zahnfabrik, or combinations thereof.

The masking composition coating on the glass ceramic can be dried by heating. In some embodiments, the holding time for the drying of the coated dental restoration is a range of about 5 sec to about 300 sec, or in a range of about 10 sec to about 180 sec, or in a range of about 20 sec to about 120 sec, or in a range of about 30 sec to about 60 sec. In some embodiments, the drying temperature for the drying of the coated dental restoration is in a range of about 20° C. to about 450° C., or in a range of about 50° C. to about 400° C., or in a range of about 80° C. to about 350° C., or in a range of about 100° C. to about 320° C., or in a range of about 120° C. to about 300° C.

In some embodiments, characterization can be deposited on the milled glass-ceramic dental restoration after the coated dental restoration is dried. In some embodiments, the characterization is selected from the group consisting of glazes, stains, structural compounds, or combinations thereof.

Other methods to prepare the masking composition comprise adding one or more liquid phase to one or more solid phase, wherein each phase comprises one or more components such as without limitation a glaze powder, an opacifier, a polymer, a polymer solution, a solvent, a colorant, a colorant solution, or combinations thereof.

In some embodiments, the components of the masking composition are stored in one or more containers. In some embodiments, the solid components of the masking composition are stored separately from the liquid components of the masking composition. In some embodiment, the masking composition is stored as a spray in a pressurized container comprising a propellant gas, sprayer, and optionally a spray flow meter.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Masking Composition Comprising 0.3 g of Zinc Oxide Powder 3.6 g of glaze powder, 0.3 g of zinc oxide powder, 1.8 g of polyethylene glycol 2000, 1.8 g of water, 0.8 g of 1 wt. % food yellow 5 dye aqueous solution were mixed. See, Table 1. The paste of the mixture was brushed on the milled unit of Ivoclar Vivadent IPS e-max CAD. The unit with the film was dried at 200° C. for 40 seconds. Once the unit was cooled, a layer of MiYo Trans A was applied and a subsequent layer of Miyo Storm was applied on a part of the unit.

Example 2

Masking Composition Comprising 0.6 g of Zinc Oxide Powder 3.6 g of glaze powder, 0.6 g of zinc oxide powder, 1.8 g of polyethylene glycol 2000, 1.8 g of water, 0.8 g of 1 wt. % acid yellow 23 dye aqueous solution were mixed. See, Table 1. The paste of the mixture was brushed on the milled unit of Ivoclar Vivadent IPS e-max CAD. The unit with the film was dried at 200° C. for 40 seconds. Once the unit was cooled, a layer of MiYo Trans A was applied and a subsequent layer of Miyo Storm was applied on a part of the unit.

Example 3

Masking Composition Comprising 0.9 g of Zinc Oxide Powder 3.6 g of glaze powder, 0.9 g of zinc oxide powder, 1.8 g of polyethylene glycol 2000, 1.8 g of water, 0.8 g of 1 wt. % food red 40 dye aqueous solution were mixed. See, Table 1. The paste of the mixture was brushed on the milled unit of Ivoclar Vivadent IPS e-max CAD. The unit with the film was dried at 200° C. for 40 seconds. Once the unit was cooled, a layer of MiYo Trans A was applied and a subsequent layer of Miyo Storm was applied on a part of the unit.

Example 4

Masking Composition Comprising 0.6 g of Titania Powder 3.6 g of glaze powder, 0.6 g of titania powder, 1.8 g of polyethylene glycol 2000, 1.8 g of water, 0.8 g of 10 wt. % Procion-™ MX Neutral Grey dye aqueous solution were mixed. See, Table 1. The paste of the mixture was brushed on the milled unit of Ivoclar Vivadent IPS e-max CAD. The unit with the film was dried at 200° C. for 40 seconds. Once the unit was cooled, a layer of MiYo Trans A was applied and a subsequent layer of Miyo Storm was applied on a part of the unit.

Example 5

Masking Composition Comprising 0.6 g of Tin Oxide Powder 3.6 g of glaze powder, 0.6 g of tin oxide powder, 1.8 g of polyethylene glycol 2000, 1.8 g of water, 0.8 g of 1 wt. % Procion™ MX Jet Black 5 dye aqueous solution were mixed. See, Table 1. The paste of the mixture was brushed on the milled unit of Ivoclar Vivadent IPS e-max CAD. The unit with the film was dried at 200° C. for 40 seconds. Once the unit was cooled, a layer of MiYo Trans A was applied and a subsequent layer of Miyo Storm was applied on a part of the unit.

TABLE 1 components from examples 1-5.

| | Solid components | | | | | | | | | Liquid components | | | | | |
|---|---|---|---|---|---|---|---|---|---|---|---|---|---|---|---|
| | Glaze powder | | Opacifier | | Glaze | Polymer | | Total | | Dye solution | | Solvent | | Total | |
| e.g. | wt. g. | % | wt. g. | % | powder: opacifier | wt. g. | % | wt. g. | % | wt. g. | % | wt. g. | % | wt. g. | % |
| 1 | 3.6 | 43 | 0.3 | 4 | 1:0.08 | 1.8 | 22 | 5.7 | 69 | 0.8 | 10 | 1.8 | 22 | 2.6 | 31 |
| 2 | 3.6 | 42 | 0.6 | 7 | 1:0.17 | 1.8 | 21 | 6.0 | 70 | 0.8 | 9 | 1.8 | 21 | 2.6 | 30 |
| 3 | 3.6 | 40 | 0.9 | 10 | 1:0.25 | 1.8 | 20 | 6.3 | 71 | 0.8 | 9 | 1.8 | 20 | 2.6 | 29 |
| 4 | 3.6 | 42 | 0.6 | 7 | 1:0.17 | 1.8 | 21 | 6.0 | 70 | 0.8 | 9 | 1.8 | 21 | 2.6 | 30 |
| 5 | 3.6 | 42 | 0.6 | 7 | 1:0.17 | 1.8 | 21 | 6.0 | 70 | 0.8 | 9 | 1.8 | 21 | 2.6 | 30 |

The layers of dried paste on the milled units from Examples 1-5 effectively masked the color of the underlying lithium-silicate material, and showed colors of the dried pastes themselves. There was no disruption of layer while the subsequent effect layer was applied. The dental restorations were fired according to the firing schedule of e-max CAD blocks. The layer with opacifiers and dyes became transparent after firing. Dissolution of opacifiers in the glazes and burning away of polymer and dyes were complete. The secondary color effects applied over the masking layer remained, and the desired characterization was achieved.

What is claimed is:

1. A method for making a coated lithium-silicate glass-ceramic dental restoration, the method comprising:

mixing a masking composition comprising:

at least one glaze powder;

at least one opacifier; and at least one colorant, to form a paste in a soft state; and coating with the paste the lithium-silicate glass-ceramic dental restoration to form the coated lithium-silicate glass-ceramic dental restoration, wherein the opacifier and colorant are designed to disappear during a crystallization cycle.

2. The method of claim 1, further comprising drying the coated lithium-silicate glass-ceramic dental restoration using heat and/or cooling the coated lithium-silicate glass-ceramic dental restoration.

3. The method of claim 2, wherein the drying temperature is in a range of about 20° C. to about 450° C., or wherein the drying time is in a range of about 5 seconds to about 300 seconds.

4. The method of claim 1, further comprising applying a characterization on the coated lithium-silicate glass-ceramic dental restoration.

5. The method of claim 4, wherein the characterization is selected from the group consisting of glazes, stains, structural compounds, or combinations thereof.

6. The method of claim 4, further comprising crystallizing the coated lithium-silicate glass-ceramic dental restoration.

7. The method of claim 6, wherein the crystallization temperature is in a range of about 500° C. to about 1,000° C.

8. The method of claim 1, wherein the at least one glaze powder comprises about 5 wt. % to about 99.9 wt. % of the masking composition.

9. The method of claim 1, wherein the at least one glaze powder comprises about 5 wt. % to about 85 wt. % of the masking composition.

10. The method of claim 1, wherein the at least one opacifier comprises about 0.1 wt. % to about 40 wt. % of the masking composition, and/or wherein the at least one opacifier is selected from the group consisting of zinc oxide, titania, tin oxide, or combinations thereof.

11. The method of claim 1, wherein the at least one glaze powder and the at least one opacifier have a ratio between about 1:0.5 to about 1:0.01.

12. The method of claim 1, wherein the at least one colorant comprises about 0.01 wt. % to about 10 wt. % of the masking composition, and/or wherein the at least one colorant is an organic dye, an organic pigment, or combination thereof.

13. The method of claim 1, wherein the masking composition further comprises at least one polymer.

14. The method of claim 13, wherein the at least one polymer is selected from the group consisting of polyethylene glycol, polypropylene glycol, polyacrylate, polymethacrylate, polyvinyl alcohol, polyvinyl butyral, polylactic acid, or combinations thereof.

15. The method of claim 13, wherein the at least one polymer comprises about 0.1 wt. % to about 80 wt. % of the masking composition.

16. The method of claim 13, wherein the at least one polymer is a polymerizable monomer, a polymerizable oligomer, a polymerizable polymer, or a combination thereof.

17. The method of claim 16, wherein the polymerizable monomer, polymerizable oligomer, and the polymerizable polymer are polymerizable with light curing, thermal curing, or a combination thereof.

18. The method of claim 13, wherein the at least one polymer is added to the masking composition directly, as a polymer solution, or combination thereof.

19. The method of claim 1, wherein the masking composition further comprises at least one solvent.

20. The method of claim 19, wherein the at least one solvent comprises equal to or less than about 95 wt. % of the masking composition, and/or wherein the at least one solvent is selected from the group consisting of water, methanol, ethanol, propanol, isopropanol, ethyl acetate, hexane, toluene, ethylene glycol, propylene glycol, butylene glycol, glycerol, polyethylene glycol, polypropylene glycol, or combinations thereof.

* * * * *